United States Patent [19]

Bacher et al.

[11] 4,363,751
[45] Dec. 14, 1982

[54] CATALYST FOR THE PREPARATION OF 4-CYANOTHIAZOLE AND PROCESS FOR PREPARING THE CATALYST

[75] Inventors: Stuart Bacher, Old Bridge; Carlos B. Rosas, Rahway; John J. Sharkey, North Brunswick, all of N.J.

[73] Assignee: Merck & Co., Inc., Rahway, N.J.

[21] Appl. No.: 262,984

[22] Filed: May 20, 1981

Related U.S. Application Data

[63] Continuation-in-part of Ser. No. 174,956, Aug. 4, 1980, abandoned.

[51] Int. Cl.³ .................. B01J 23/14; B01J 23/26; B01J 23/28; B01J 23/34
[52] U.S. Cl. .................. 252/469; 252/467; 548/198
[58] Field of Search ............... 252/467, 469; 423/595, 423/598; 548/198

[56] References Cited

U.S. PATENT DOCUMENTS

| | | | |
|---|---|---|---|
| 3,198,750 | 8/1965 | Callahan et al. | 252/456 |
| 3,435,069 | 3/1969 | Bethell et al. | 252/467 X |
| 3,595,961 | 7/1971 | Stahle et al. | 424/273 |
| 3,636,219 | 1/1972 | Culik et al. | 424/265 |
| 3,642,930 | 2/1972 | Grasselli et al. | 585/608 |
| 3,666,822 | 5/1972 | Grasselli et al. | 585/626 |
| 3,937,717 | 2/1976 | Stahle et al. | 548/316 |
| 3,988,345 | 10/1976 | Franzmair | 548/315 |
| 4,003,978 | 1/1977 | Shiraishi et al. | 252/467 X |
| 4,055,511 | 10/1977 | Elion et al. | 252/435 |
| 4,055,514 | 10/1977 | Elion et al. | 252/470 |

Primary Examiner—W. J. Shine
Attorney, Agent, or Firm—David L. Rose; Mario A. Monaco

[57] ABSTRACT

An improved process for the preparation of 4-cyanothiazole from 4-methylthiazole using an ammoxidation catalyst composed of manganese, chromium and molybdenum is disclosed.

17 Claims, No Drawings

CATALYST FOR THE PREPARATION OF 4-CYANOTHIAZOLE AND PROCESS FOR PREPARING THE CATALYST

CROSS REFERENCE TO RELATED APPLICATIONS

This application is a continuation-in-part of our copending application Ser. No. 174,956 filed Aug. 4, 1980, now abandoned.

BACKGROUND OF THE DISCLOSURE

One of the problems inherent in an ammoxidation system for making cyanothiazole from 4-methylthiazole in a system employing excess oxygen in the reactant stream is undesirable combustion of the organic reactant and ammonia to unwanted by-products. This, of course, adds to process costs in that more reactant is required to produce a given amount of cyano compound (e.g., yields are reduced) and also larger capital investment is required to build a plant for a given capacity. Thus, a reduction in the undesired combustion of ammonia and organic reactant with the attendant yield increase is a desirable objective. The instant process overcomes these difficulties and provides for a more efficient, more selective and more economic process.

SUMMARY OF THE INVENTION

The instant invention consists of an improved process for preparing 4-cyanothiazole from 4 methylthiazole wherein the ammoxidation process utilizes a new catalyst composed of oxides of manganese, chromium and molybdenum. Thus, it is an object of this invention to describe such an improved process. A further object of this invention is to describe the novel catalyst utilized in such process. A still further object is to describe the procedures used for making such a catalyst. Further objects will become apparent from reading the following description.

DESCRIPTION OF THE INVENTION

It has now been found that in the catalytic vapor phase ammoxidation of 4-methylthiazole to 4-cyanothiazole, the yield of 4-cyanothiazole can be significantly increased, and ammonia and thiazole decomposition mitigated, by utilizing as catalyst the novel catalyst composition described herein. An advantage of the present invention is that the catalyst is more selective for production of the desired 4-cyanothiazole.

Another advantage is that an adiabatic or isothermal type reactor can be utilized without any significant decrease in the high selectivity for 4-cyanothiazole.

In accordance with the invention, there is provided a process for the preparation of 4-cyanothiazole from 4-methylthiazole which comprises passing, as a reactant stream over the novel catalyst, a gaseous mixture comprising:
(1) 4-methylthiazole;
(2) ammonia;
(3) oxygen; and
(4) water as steam.

The improvement comprises passing said gaseous reactant stream through a reactor containing the improved catalyst at a temperature of from 360° to 480° C.

The novel catalyst consists of a mixture of metal oxides with the following emperical formula:

$$Mn_a Cr_b Mo_{1.00} O_x$$

wherein a and b can be from 0.02 to 15 but the sum of a and b cannot be less than 0.8. The term x is a number which satisfies the valence requirements of the metallic elements present in the catalyst. It is preferred to utilize a catalyst wherein the values of a and b are between 0.5 and 4.0 and the sum of a and b is not less than 1.0.

If desired, a reaction promoter can be added to the catalyst mixture to improve the activity and selectivity of the catalyst. The preferred promoter is tin. The level of tin present in the catalyst may be from 0.0 to 10% by weight. The preferred level of tin is from about 0.1% to 1.0% by weight.

One method of preparing the catalyst is by dissolving water soluble molybdenum, chromium and manganese salts in water, drying and calcining. The preferred salt for molybdenum is ammonium heptamolybdate. The preferred salts for chromium and manganese are the nitrates. If tin is to be added as a reaction promoter, it is preferred to use stannic chloride. When the metal salts are all dissolved in water, generally only a minimum amount of water is used. The aqueous solution is then dried. The solution may be concentrated to a viscous solution and air dried, however, spray drying is preferred. Generally, to improve the handling of the dried material, particularly during the subsequent tableting operations, a binding agent is added to the mixture such as silica in the form of silicon dioxide. An aqueous colloidal silicon dioxide such as Ludox AS-40 is very satisfactory. The preferred level of silica is 20% by weight of the calcined catalyst. After drying, the dried material is then calcined to form the metal oxide mixture. The calcining is generally carried out in a forced air oven at about 450° C. for about 16 hours.

To improve the catalyst, by providing increased physical strength, the dried material is generally compressed into shapes, such as tablets or pellets, prior to calcining. It is preferred to compress the dried material into cylindrically shaped tablets for improved performance in the ammoxidation reactor. While the size of the tablets can vary with the size of the reactor. Tablets of from 2.0 to 4.0 mm in diameter and a thickness of from 1.0 to 4.0 mm are preferred wherein such tablets may weigh from about 20 to 40 mg.

It is often preferred to add a lubricant to the dried powder prior to tableting. Graphite is suitable and may be added in amounts up to about 1 to 5 g of graphite per 100 g of catalyst. It is preferred to use 1% graphite.

The catalyst may also be strengthened by impregnating a support with such catalyst. Suitable for such supported catalysts are silica and kieselguhr.

Another such method is the use of a coated catalyst wherein the catalyst is deposited completely around and adhered to an inert support. This technique is well-known to those skilled in this art and U.S. Pat. No. 4,077,912 discloses methods useful for preparing such catalysts.

In addition, to the above, other methods of catalyst preparation known to those skilled in the art may be employed. One such method is co-precipitation. The normal co-precipitation techniques, causing precipitation by adjusting the pH with acid or base are preferred.

After the catalyst is prepared, it is charged into a suitable reactor. Generally, a packed bed reactor is employed. A gaseous stream consisting of 4-methylthiazole, ammonia, air and water vapor is then continuously passed over the heated catalyst. The preferred concentration of 4-methylthiazole in the reaction stream is 0.5 to 1.2 mole percent. The preferred mole ratios of the other reactants are:
Oxygen: 4-methylthiazole = 16:1 to 32:1
Ammonia: 4-methylthiazole = 1:1 to 2:1
Water: 4-methylthiazole = 0 to 10:1

For an isothermal reaction system employing a tableted, tin promoted catalyst with silica, a temperature range of from 360° to 480° C. is employed. A preferred temperature range is from 410° to 455° C. For other catalyst preparations, such as granular, non-tableted systems with or without one or both of tin and silica, the temperature ranges can be adjusted upwards or downwards by about 60° C. Similar shifts in the preferred ranges would be observed.

Where non-tableted catalysts are employed, the catalyst is ground and passed through a series of graduated sieves to provide for a uniform range of sizes. The sizes of particles used in a particular reactor will depend upon the size of the reactor, with larger reactors generally requiring larger particle sizes. For reactors generally used for investigational purposes particle sizes of from 16 to 30 mesh are particularly suitable.

The contact time for the reaction is from 0.04 to 1.7 grams of catalyst-seconds per ml of reaction stream. A preferred reaction contact time is from 0.25 to 0.35 grams of catalyst-seconds per ml of reaction stream.

The product of this process, 4-cyanothiazole is an important chemical intermediate, useful in the preparation of many different compounds. One of the most important products prepared from 4-cyanothiazole is thiabendazole (2-(4'-thiazolyl)benzimidazole). Thiabendazole is an important anthelmintic and fungicidal agent very familiar to those skilled in the arts of veterinary medicine, animal husbandry, and agricultural fungicides. The compound is also an important industrial fungicide with uses in the paint industry and in circulating water systems such as in cooling towers and in the paper industry.

The following examples are provided in order that the invention might be illustrated and more fully understood. They are not to be construed as limitative of the invention.

EXAMPLE 1

The Preparation and Performance of a Typical Unpromoted Catalyst

With agitation 74.7 gms of 53.4% Mn $(NO_3)_2$ solution and 106.0 gms of Cr $(NO_3)_3.9H_2O$ are added to 52 mls of distilled water. The mixture is aged at 25°–30° C. until nearly complete dissolution occurs. Then it is filtered to remove insoluble impurities.

To 76 mls of distilled water is added, with agitation, 46.8 gms of $(NH_4)_6Mo_7O_{24}.4H_2O$. After the addition, the mixture is heated to 42°–47° C. and aged until essentially all the material is dissolved. Then, to remove insoluble particulate matter, the mixture is filtered.

Over a 30 minute period, the manganese and chromium nitrate solution is added, with continuous agitation, to the molybdate solution. After aging an additional 30 minutes at 25°–30° C., the combined solutions are concentrated by heating until a viscous fluid is obtained. The resultant material is then dried at 120° C. in a forced air oven to a moisture content of less than 5%.

The dried catalyst is calcined in air at 450° C. for 16 hours. After calcining, it is crushed and screened to 16–30 mesh material. The mole ratio of Mn:Cr:Mo in the final catalyst is 0.84:1.00:1.00.

Three and six-tenths cubic centimeters (3.6 cc) of the catalyst, prepared in accordance with the procedure described above, are placed into a 0.635 centimeter (cm) inside diameter (ID) stainless steel reactor tube. The reactor tube is heated electrically and connected via a suitable sampling system to a gas chromatograph for analysis of the reactants and products. The reactor feed is comprised of air, 4-methylthiazole, ammonia and water in the ratio of 28:1:1.5:3.1. The flow rates are adjusted to provide a total flow of 720 cc/min and, thus, a contact time of 0.27 gm of catalyst -seconds per ml of reaction stream. The reactor temperature is maintained at 442° C. At this temperature, 39% of the 4-methylthiazole is converted into products. Of the 4-methylthiazole converted, 74% is converted to 4-cyanothiazole (RCN), 7.3% is converted to thiazole (RH) and the remainder is converted to combustion products. Thus, the selectivity to the desired product, 4-cyanothiazole, is 74%. The conversion and selectivity to 4-cyanothiazole and thiazole at other temperatures are given in Table I.

TABLE I

Catalyst: $Mn_{0.84}Cr_{1.00}Mo_{1.00}O_{5.34}$

| Temp (°C.) | Conversion (%) | Selectivity (%) | |
|---|---|---|---|
| | | RCN | RH |
| 411 | 13 | 71 | 8.2 |
| 424 | 18 | 74 | 7.1 |
| 442 | 39 | 74 | 7.3 |
| 457 | 62 | 74 | 8.2 |
| 476 | 88 | 68 | 10.5 |
| 495 | 99 | 56 | 12.4 |

EXAMPLE 2

The Preparation and Performance of a Tin Promoted Catalyst

With agitation, 79.8 gms of 53.4% $Mn(NO_3)_2$ solution, 106.0 gms of $Cr(NO_3)_3.9H_2O$ and 1.088 gms of $SnCl_4.5H_2O$ are added to 47 mls of distilled water. The mixture is aged at 25°–30° C. until complete dissolution results.

To 76 mls of distilled water is added, with agitation, 46.8 gms of $(NH_4)_6Mo_7O_{24}.4H_2O$. After the addition, the mixture is heated to 42°–47° C. and aged until essentially all the material is dissolved. Then, to remove insoluble particulate matter, it is filtered.

Over a 30 minute period, the solution containing manganese nitrate, chromium nitrate and stannic chloride is added, with continuous agitation, to the molybdate solution. After aging an additional 30 minutes at 25°–30° C., the combined solutions are concentrated by heating until a viscous fluid is obtained. The resultant material is then dried at 120° C. in a forced air oven to a moisture content of less than 5%.

The dried catalyst is calcined in air at 450° C. for 16 hours. After calcining, it is crushed and screened to 16–30 mesh material. The mole ratio of Sn:Mn:Cr:Mo in the final catalyst is 0.012:0.90:1.00:1.00. By weight, the tin is present to the extent of 0.5%.

The reactor conditions and feed composition employed for this catalyst are the same as those utilized in Example 1. The conversion and selectivity to 4-cyanothiazole and thiazole are given in Table II.

TABLE II

Catalyst: $Sn_{0.012}Mn_{0.90}Cr_{1.00}Mo_{1.00}O_{5.42}$

| Temp (°C.) | Conversion (%) | Selectivity (%) RCN | RH |
|---|---|---|---|
| 410 | 34 | 76 | 2.9 |
| 426 | 44 | 77 | 2.7 |
| 441 | 63 | 78 | 3.0 |
| 457 | 80 | 72 | 8.4 |
| 475 | 92 | 65 | 9.7 |
| 492 | 98 | 51 | 9.0 |

EXAMPLE 3

The Preparation and Performance of a Tin Promoted Catalyst Which Contains Silica With agitation 8444.9 gms of $Cr(NO_3)_3.9H_2O$ is added to 1602 mls of distilled water held at 65°–70° C. After the $Cr(NO_3)_3.9H_2O$ dissolves and while still maintaining a temperature of 65°–70° C., 4795.9 gms of molten 70.8% $Mn(NO_3)_2$ is added.

To 6055 mls of distilled water is added, with agitation, 3728.5 gms of $(NH_4)_6Mo_7O_{24}.4H_2O$. After the addition, the mixture is heated to 42°–47° C. and aged until essentially all the material is dissolved. Then, to remove insoluble particulate matter, it is filtered. After the filtration, the filtrate is heated to 65°–70° C. and to it is added 88.6 gms of $SnCl_4.5H_2O$.

Over a 60 minute period, the chromium and manganese nitrate solution is added, with continuous agitation, to the molybdate solution containing the stannic chloride. During the addition, both solutions are maintained at 65°–70° C. After they are combined, the solutions are heated to 100°–105° C. When all the solids have dissolved, 3768.3 gms of Ludox AS-40 is added. The resultant solution, held at 100°–105° C., is then spray dried to obtain a powder at a temperature of 80° C. or greater and with a moisture content of less than 5%.

After spray drying, the powder is blended with a lubricating graphite (1 gm of graphite per 20 gms of spray dried powder) and compressed into tablets of a size of about 3.2 mm in diameter and 3.2 mm thick weighing from 20 to 40 mg each. The tablets are then calcined in air at 450° C. for 16 hours.

When the calcination is complete, the catalyst is ready for use. However, for evaluation, the catalyst is normally crushed and screened to 16–30 mesh material. The mole ratio of Sn:Mn:Cr:Mo in the final catalyst is 0.012:0.90:1.00:1.00. The level of $SiO_2$ is about 19% by weight.

The reactor conditions and feed composition employed for this catalyst are the same as those utilized in Example 1. The conversion and selectivity to 4-cyanothiazole and thiazole are given in Table III.

TABLE III

Catalyst: $Sn_{0.012}Mn_{0.90}Cr_{1.00}Mo_{1.00}O_{5.42}$ (81%)-$SiO_2$ (19%)

| Temp (°C.) | Conversion (%) | Selectivity (%) RCN | RH |
|---|---|---|---|
| 394 | 13 | 71 | 8.3 |
| 409 | 20 | 75 | 6.9 |
| 425 | 29 | 75 | 6.3 |
| 440 | 47 | 74 | 6.6 |
| 455 | 71 | 74 | 7.3 |
| 474 | 93 | 67 | 8.9 |

EXAMPLE 4

The Preparation of a Catalyst With Reduced Tin and Graphite and Without Silica.

A spray dried powder is prepared as outlined in Example 3. It contains the same amounts of manganese, chromium and molybdenum as in Example 3, but three-fifths of the tin and no Ludox. After preparation, the powder is blended with a lubricating graphite (1 gm per 100 gm of spray dried powder) and compressed into suitably shaped tablets. The tablets are next calcined in air by heating to 450° C. over an 8 hour period and aging at this temperature for an additional 8 hours.

When the calcination is complete, the tableted catalyst is ready for use. However for evaluation, the catalyst is normally crushed and screened to 16–30 mesh material. The mole ratio of Sn:Mn:Cr:Mo in the final catalyst is 0.0072:0.90:1.00:1.00. This represents 0.3% of tin by weight.

The reactor conditions and feed composition employed for this catalyst are the same as those utilized in Example 1. The conversion and selectivity to 4-cyanothiazole and thiazole are given in Table IV.

TABLE IV

Catalyst: $Sn_{0.0072}Mn_{0.90}Cr_{1.00}Mo_{1.00}O_{5.41}$

| Temp (°C.) | Conversion (%) | Selectivity (%) RCN | RH |
|---|---|---|---|
| 380 | 14 | 51 | 1.3 |
| 395 | 22 | 65 | 2.8 |
| 411 | 34 | 73 | 2.4 |
| 429 | 51 | 77 | 2.5 |
| 445 | 69 | 77 | 3.3 |
| 460 | 89 | 73 | 4.9 |
| 476 | 97 | 64 | 5.8 |

EXAMPLE 5

The Preparation and Performance of a Coprecipitated Unpromoted Catalyst

With agitation 79.8 gms of 54.9% $Mn(NO_3)_2$ solution and 106.0 gms of $(Cr(NO_3)_3.9H_2O$ are added to 47.0 mls of distilled water. The mixture is aged at 25°–30° C. until nearly complete dissolution occurs. Then it is filtered to remove insoluble impurities.

To 76 mls of distilled water is charged, with agitation, 46.8 gms of $(NH_4)_6Mo_7O_{24}.4H_2O$. After addition, the mixture is heated to 42°–47° C. and aged until essentially all the material is dissolved. Then, to remove insoluble particulate matter, it is filtered.

Over a 60 min period, the manganese and chromium nitrate solution is added, with continuous agitation, to the molybdate solution. 15 N $NH_4OH$ is then added until the pH remains at 5.5 to 5.8 for 60 minutes. About 72 mls of ammonium hydroxide is required.

The precipitate obtained is filtered and washed with 280 mls of distilled water. After washing, the filter cake is dried at 120° C. in a forced air oven to a moisture content of less than 5%.

The dried catalyst is calcined in air at 450° C. for 16 hours. After calcining, it is crushed and screened to 16–30 mesh material. The mole ratio of Mn:Cr:Mo in the final catalyst is 0.90:1.00:1.00.

The reactor conditions and feed composition employed for this catalyst are the same as those utilized in Example 1. The conversion and selectivity to 4-cyanothiazole and thiazole are given in Table V.

TABLE V

Catalyst: $Mn_{0.90}Cr_{1.00}Mo_{1.00}O_{5.40}$

| Temp (°C.) | Conversion (%) | Selectivity (%) RCN | Selectivity (%) RH |
|---|---|---|---|
| 384 | 17 | 67 | 9.6 |
| 400 | 26 | 66 | 8.6 |
| 416 | 40 | 74 | 7.5 |
| 432 | 58 | 75 | 6.9 |
| 440 | 75 | 77 | 3.3 |
| 446 | 82 | 72 | 8.6 |
| 461 | 96 | 64 | 11.1 |

EXAMPLE 6

The Preparation and Performance of a Coated Catalyst

A spray dried powder is prepared as outlined in Example 3. It contains the same amounts of manganese, chromium and molybdenum as in Example 3, but one-fifth the amount of tin and no Ludox. After preparation, the spray dried powder is calcined in air by heating to 450° C. over an 8 hour period and then aging at this temperature for an additional 8 hours. Once calcined, it is then passed through a 100 mesh screen. The mole ratio of Sn:Mn:Cr:Mo in the final fired powder is 0.0024:0.90:1.00:1.00. This represents 0.1% of tin by weight.

To a slowly rotating inclined glass container is next charged, 40.1 gms of 16-30 mesh alundum (Norton SA-5123), 7.5 gms of silica (DuPont Ludox AS-40) and 10.0 gms of the fired catalyst powder prepared above. Prior to the addition, the Ludox and fired catalyst powder are divided into 3 approximately equal parts. Each part is added alternately to the gently tumbling alundum over a 60 minute period.

Once the addition is complete, the contents of the glass container are blended an additional 15 minutes and then transferred to a porcelain evaporating dish. After air drying at 120° C. for 16 hours, the final coated support is gently screened to 12-30 mesh material. The amount of fired catalyst powder and $SiO_2$ in the final coated support is 11.5% and 3.4%, respectively.

The reactor conditions and feed composition employed for this coated support are the same as those utilized in Example 1. The conversion and selectivity to 4-cyanothiazole and thiazole are given in Table VI.

TABLE VI

Catalyst: $Sn_{0.0024}Mn_{0.90}Cr_{1.00}Mo_{1.00}O_{5.40}$ (11.5 wt %)
$SiO_2$ (3.4 wt %)
Alundum (85.1 wt %)

| Temp (°C.) | Conversion (%) | Selectivity (%) RCN | Selectivity (%) RH |
|---|---|---|---|
| 410 | 5 | 5 | 0.1 |
| 426 | 7 | 21 | 0.1 |
| 440 | 10 | 55 | 0.1 |
| 456 | 17 | 58 | 0.1 |
| 469 | 25 | 66 | 2.3 |
| 484 | 38 | 70 | 2.5 |
| 505 | 53 | 72 | 3.1 |

What is claimed is:

1. An ammoxidation catalyst which consists of manganese, chromium and molybdenum oxides in the molecular ratios of: $Mn_aCr_bMo_{1.00}O_x$ wherein a and b are from 0.02 to 15 provided the sum of a and b is not less than 0.8 and x is a number which satisfies the valences of the metallic elements.

2. The catalyst of claim 1 wherein a and b are from 0.5 to 4.0 and the sum of a and b is not less than 1.0.

3. The catalyst of claim 2 which has the molecular formula of $Mn_{0.90}Cr_{1.00}Mo_{1.00}O_{5.40}$.

4. The catalyst of claim 1 which also includes from 0.0 to 10% by weight of tin as the oxide.

5. The catalyst of claim 4 wherein the tin is present at from about 0.1 to 1.0% by weight.

6. The catalyst of claim 5 which has the molecular formula of $Sn_{0.012}Mn_{0.90}Cr_{1.00}Mo_{1.00}O_{5.42}$.

7. The catalyst of claim 5 which has the molecular formula of $Sn_{0.0072}Mn_{0.90}Cr_{1.00}Mo_{1.00}O_{5.41}$.

8. An ammoxidation catalyst which consists of manganese, chromium and molybdenum oxides in the molecular ratio of: $Mn_aCr_bMo_{1.00}O_x$ wherein a and b are from 0.02 to 15 provided the sum of a and b is not less than 0.8, and x is a number which satisfies the valence of the metallic elements, prepared by dissolving soluble salts of manganese, chromium and molybdenum in water, drying the aqueous mixture and calcining the dried material at about 450° C. for about 16 hours.

9. The catalyst of claim 8 wherein a and b are from 0.5 to 4.0 and the sum of a and b is not less than 1.0.

10. The catalyst of claim 9 which has the molecular formula of $Mn_{0.90}Cr_{1.00}Mo_{1.00}O_{5.40}$.

11. The catalyst of claim 8 which also includes from 0.0 to 10% by weight of tin as the oxide.

12. The catalyst of claim 9 wherein the tin is present at from 0.1 to 1.0% by weight.

13. The catalyst of claim 12 which has the molecular formula of: $Sn_{0.012}Mn_{0.90}Cr_{1.00}Mo_{1.00}O_{5.42}$.

14. The catalyst of claim 12 which has the molecular formula of: $Sn_{0.0072}Mn_{0.90}Cr_{1.00}Mo_{1.00}O_{5.41}$.

15. A process for preparing the catalyst of claim 1 which comprises dissolving water soluble salts of manganese, chromium and molybdenum in water, evaporating the water, and calcining the resultant dried material at about 450° C. for about 16 hours.

16. The process of claim 15 wherein the manganese and chromium salts are in the form of the nitrates and the molybdenum salt is in the form of ammonium heptamolybdate.

17. The process of claim 16 wherein the water soluble salts also include stannic chloride.

* * * * *